United States Patent
Ramanujam et al.

(10) Patent No.: US 10,047,022 B2
(45) Date of Patent: Aug. 14, 2018

(54) PROCESS AND APPARATUS FOR SEPARATING C5 DI-OLEFINS FROM PYROLYSIS GASOLINE

(71) Applicant: GTC Technology US LLC, Houston, TX (US)

(72) Inventors: Venkata K. Ramanujam, Sugar Land, TX (US); B. Bryant Slimp, Jr., Houston, TX (US); Cole Nelson, Cypress, TX (US); Michael McCaulley, Sugar Land, TX (US)

(73) Assignee: GTC Technology US LLC, Houston, TX (US)

(*) Notice: Subject to any disclaimer, the term of this patent is extended or adjusted under 35 U.S.C. 154(b) by 220 days.

(21) Appl. No.: 14/297,412

(22) Filed: Jun. 5, 2014

(65) Prior Publication Data

US 2014/0364665 A1    Dec. 11, 2014

Related U.S. Application Data

(60) Provisional application No. 61/831,447, filed on Jun. 5, 2013.

(51) Int. Cl.

| C07C 7/08 | (2006.01) |
|---|---|
| C07C 2/50 | (2006.01) |
| C07C 7/00 | (2006.01) |
| B01D 3/00 | (2006.01) |
| C07C 7/04 | (2006.01) |

(Continued)

(52) U.S. Cl.
CPC .............. *C07C 7/005* (2013.01); *B01D 3/009* (2013.01); *B01D 3/40* (2013.01); *C07C 2/50* (2013.01); *C07C 7/04* (2013.01); *C07C 7/10* (2013.01); *C10G 7/02* (2013.01); *C07C 2603/68* (2017.05); *C10G 2300/104* (2013.01); *C10G 2300/1044* (2013.01); *C10G 2400/02* (2013.01)

(58) Field of Classification Search
None
See application file for complete search history.

(56) References Cited

U.S. PATENT DOCUMENTS 2,436,149 A * 2/1948 Menshih .................. C07C 7/17
568/28
2,582,920 A * 1/1952 Businger .................. C07C 4/22
422/131

(Continued)

FOREIGN PATENT DOCUMENTS

GB           1340149 A  * 12/1973    ............... C07C 7/08

*Primary Examiner* — Philip Y Louie
(74) *Attorney, Agent, or Firm* — Winstead PC

(57) ABSTRACT

Apparatuses, systems and methods for producing Pips stream for manufacturing catalytic C5 hydrocarbon resins containing all the key reactive monomers that are already present in the C5 fraction of the pyrolysis gasoline, which is otherwise lost with the crude isoprene stream, are disclosed herein. Embodiments of the invention are directed to producing a hydrocarbon resin grade DCPD stream consisting of dimers and codimers of isoprene which are of value in manufacturing thermal hydrocarbon resins, either polymer grade isoprene and gasoline quality raffinate (free or sulfur and acetylenes) or a relatively small crude isoprene stream with maximum utilization of isoprene by moving some of the isoprene to a DCPD stream used to manufacture thermal hydrocarbon resins.

11 Claims, 4 Drawing Sheets

(51) Int. Cl.
*C07C 7/10* (2006.01)
*B01D 3/40* (2006.01)
*C10G 7/02* (2006.01)

(56) References Cited

U.S. PATENT DOCUMENTS

| | | | | |
|---|---|---|---|---|
| 3,097,249 | A * | 7/1963 | Marchant | C07C 7/17 585/2 |
| 3,196,188 | A * | 7/1965 | Parrish | C07C 2/50 585/362 |
| 3,301,915 | A * | 1/1967 | King | C07C 7/005 203/28 |
| 3,510,405 | A * | 5/1970 | Koide | C07C 7/08 203/60 |
| 3,557,239 | A | 1/1971 | Gebhart, Jr. et al. | |
| 3,775,259 | A | 11/1973 | Sarno | |
| 4,081,332 | A * | 3/1978 | Hein | C07C 7/08 203/51 |
| 4,147,848 | A * | 4/1979 | Arakawa | C07C 7/05 203/70 |
| 5,401,891 | A * | 3/1995 | Keenan | C07C 2/44 585/318 |
| 6,258,989 | B1 * | 7/2001 | Owen | C10G 65/06 208/211 |
| 8,066,868 | B1 | 11/2011 | Zimmermann | |
| 2003/0100809 | A1 * | 5/2003 | Tian | C07C 7/005 585/362 |
| 2004/0049093 | A1 | 3/2004 | Cheung et al. | |
| 2011/0178349 | A1 * | 7/2011 | Anzick | C07C 7/177 585/318 |

\* cited by examiner

| STREAM DESCRIPTION | M1 | M2A | M2 | M3 | M4 | M4A | M5 | M5A | M6 | M7 | M8 | M9 | M10 | M11 | M12 |
|---|---|---|---|---|---|---|---|---|---|---|---|---|---|---|---|
| PHASE | LIQUID | LIQUID | LIQUID | LIQUID | LIQUID | LIQUID | LIQUID | LIQUID | LIQUID | LIQUID | LIQUID | MIXED | LIQUID | LIQUID | LIQUID |
| TOTAL MOLAR RATE KG-MOL/HR | 293 | 51 | 242 | 226 | 107 | 104 | 59 | 59 | 37 | 120 | 50 | 52 | 15 | 89 | 15 |
| TOTAL WEIGHT COMPOSITION PERCENT | | | | | | | | | | | | | | | |
| C4's | 3.63 | 21.64 | 0.03 | 0.03 | 0.00 | 0.00 | 0.00 | 0.00 | 0.00 | 0.06 | 0.15 | 0.25 | 0.00 | 0.08 | 0.00 |
| 14PNDIEN | 1.01 | 4.52 | 0.31 | 0.29 | 0.00 | 0.00 | 0.00 | 0.00 | 0.00 | 0.62 | 0.05 | 0.00 | 0.00 | 0.81 | 0.00 |
| I-PENTANE | 10.35 | 49.61 | 2.50 | 2.36 | 0.00 | 0.00 | 0.00 | 0.00 | 0.00 | 5.09 | 0.00 | 5.25 | 0.00 | 9.51 | 0.09 |
| 1PENTENE | 3.20 | 10.37 | 1.76 | 1.67 | 0.00 | 0.00 | 0.00 | 0.00 | 0.00 | 3.59 | 0.01 | 0.01 | 0.00 | 4.77 | 0.00 |
| 2M1BUTENE | 4.03 | 10.33 | 2.78 | 2.62 | 0.00 | 0.03 | 0.06 | 0.06 | 0.00 | 5.65 | 0.01 | 0.01 | 0.01 | 7.51 | 0.00 |
| T2PENTENE | 1.76 | 0.05 | 2.11 | 1.99 | 0.03 | 0.03 | 0.06 | 0.06 | 0.00 | 4.26 | 0.01 | 0.01 | 0.01 | 5.66 | 0.00 |
| C2PENTENE | 0.94 | 0.01 | 1.12 | 1.06 | 0.09 | 0.09 | 0.22 | 0.22 | 0.00 | 2.18 | 0.01 | 0.01 | 0.02 | 2.90 | 0.00 |
| ISOPRENE | 15.21 | 0.50 | 18.14 | 16.86 | 0.40 | 0.37 | 0.89 | 0.89 | 0.00 | 35.84 | 93.88 | 88.92 | 81.10 | 15.07 | 99.89 |
| PENTANE | 16.07 | 0.10 | 19.27 | 18.33 | 1.03 | 1.03 | 2.43 | 2.43 | 0.00 | 38.30 | 0.00 | 0.78 | 2.43 | 51.01 | 0.01 |
| EOPENTANE | 0.00 | 0.00 | 0.00 | 0.00 | 0.00 | 0.00 | 0.00 | 0.00 | 0.00 | 0.06 | 0.00 | 0.00 | 0.00 | 0.00 | 0.00 |
| M12BUTENE | 0.28 | 0.00 | 0.34 | 0.34 | 0.58 | 0.58 | 1.37 | 1.37 | 0.00 | 0.62 | 0.10 | 0.10 | 0.34 | 0.02 | 0.00 |
| 2M2BUTENE | 2.41 | 0.00 | 2.89 | 2.75 | 3.41 | 3.41 | 8.04 | 8.04 | 0.00 | 2.00 | 0.14 | 0.12 | 0.42 | 2.59 | 0.00 |
| 3M1BUTENE | 0.47 | 2.81 | 0.01 | 0.01 | 0.00 | 0.00 | 0.00 | 0.00 | 0.00 | 0.01 | 0.00 | 0.00 | 0.00 | 0.02 | 0.00 |
| 1PENTYNE | 0.20 | 0.00 | 0.24 | 0.23 | 0.36 | 0.36 | 0.85 | 0.85 | 0.00 | 0.07 | 0.18 | 0.00 | 0.00 | 0.00 | 0.00 |
| 2PENTYNE | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| 1P3YNE | 0.00 | 0.05 | 0.11 | 0.11 | 0.00 | 0.00 | 0.00 | 0.00 | 0.00 | 0.23 | 0.55 | 0.00 | 0.00 | 0.00 | 0.00 |
| 2M1B3YNE | 0.10 | 0.00 | 0.00 | 0.00 | 0.00 | 0.00 | 0.00 | 0.00 | 0.00 | 0.00 | 0.00 | 0.00 | 0.00 | 0.00 | 0.00 |
| 1P4YNE | 0.00 | 0.00 | 0.00 | 0.00 | 0.00 | 0.00 | 0.00 | 0.00 | 0.00 | 0.01 | 0.07 | 0.00 | 0.00 | 0.00 | 0.00 |
| C13PND | 3.81 | 0.00 | 4.57 | 4.32 | 8.04 | 8.04 | 18.11 | 18.11 | 0.00 | 0.03 | 0.45 | 1.58 | 0.00 | 0.00 | 0.00 |
| T13PND | 6.60 | 0.00 | 7.92 | 7.49 | 13.82 | 13.82 | 31.83 | 31.83 | 0.00 | 0.18 | 4.31 | 1.58 | 5.43 | 0.02 | 0.00 |
| CD13 | 18.10 | 0.01 | 21.71 | 3.07 | 4.20 | 0.34 | 0.78 | 0.78 | 0.00 | 1.77 | 0.00 | 0.00 | 0.00 | 0.00 | 0.00 |
| 23PD | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |

FIG. 3

| STREAM DESCRIPTION | M1 | M2A | M2 | M3 | M4 | M4A | M5 | M5A | M6 | M7 | M8 | M9 | M10 | M11 | M12 |
|---|---|---|---|---|---|---|---|---|---|---|---|---|---|---|---|
| 12PD | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| CYPENTEN | 4.08 | 0.00 | 4.90 | 4.63 | 8.60 | 8.60 | 19.05 | 19.05 | 0.00 | 0.05 | 0.11 | 0.02 | 0.08 | 0.01 | 0.00 |
| CP | 3.17 | 0.00 | 3.80 | 4.15 | 7.75 | 7.75 | 15.43 | 15.43 | 0.00 | 0.00 | 0.00 | 2.96 | 10.17 | 0.00 | 0.00 |
| C6+ | 0.53 | 0.00 | 0.64 | 0.61 | 1.13 | 1.13 | 0.95 | 0.95 | 0.00 | 0.00 | 0.00 | 0.00 | 0.00 | 0.00 | 0.00 |
| DCPD | 4.03 | 0.00 | 4.84 | 22.14 | 41.33 | 45.19 | 0.00 | 0.00 | 83.65 | 0.00 | 0.00 | 0.00 | 0.00 | 0.00 | 0.00 |
| C9+ | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| SOLVENT | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| CS2 | 0.08 | 0.00 | 0.10 | 0.17 | 0.16 | 0.16 | 0.32 | 0.00 | 0.00 | 0.19 | 0.44 | 0.00 | 0.00 | 0.00 | 0.00 |
| ISOPDIMER1 | 0.00 | 0.00 | 0.00 | 1.53 | 2.85 | 2.86 | 0.00 | 0.00 | 5.45 | 0.00 | 0.00 | 0.00 | 0.00 | 0.00 | 0.00 |
| CPD-ISOP#3 | 0.00 | 0.00 | 0.00 | 0.29 | 0.53 | 0.54 | 0.00 | 0.00 | 1.03 | 0.00 | 0.00 | 0.00 | 0.00 | 0.00 | 0.00 |
| ISOPDIMER3 | 0.00 | 0.00 | 0.00 | 1.53 | 2.86 | 2.87 | 0.00 | 0.00 | 5.06 | 0.00 | 0.00 | 0.00 | 0.00 | 0.00 | 0.00 |
| CPD-ISOP#2 | 0.00 | 0.00 | 0.00 | 0.07 | 0.13 | 0.13 | 0.00 | 0.00 | 0.24 | 0.00 | 0.00 | 0.00 | 0.00 | 0.00 | 0.00 |
| ISOPDIMER5 | 0.00 | 0.00 | 0.00 | 1.53 | 2.86 | 2.86 | 0.00 | 0.00 | 4.57 | 0.00 | 0.00 | 0.00 | 0.00 | 0.00 | 0.00 |
| CPD-PIP#3 | 0.00 | 0.00 | 0.00 | 0.00 | 0.00 | 0.00 | 0.00 | 0.00 | 0.00 | 0.00 | 0.00 | 0.00 | 0.00 | 0.00 | 0.00 |
| TOTAL | 100 | 100 | 100 | 100 | 100 | 100 | 100 | 100 | 100 | 100 | 100 | 100 | 100 | 100 | 100 |

FIG. 3 continued

PROCESS AND APPARATUS FOR SEPARATING C5 DI-OLEFINS FROM PYROLYSIS GASOLINE

CROSS-REFERENCES TO RELATED APPLICATIONS

This Application claims the benefit under 35 U.S.C. § 119(e) of U.S. Provisional Patent Application No. 61/831,447 filed Jun. 5, 2013 which is incorporated herein by reference in its entirety as if fully set forth herein.

BACKGROUND OF THE INVENTION

Pyrolysis gasoline produced from liquid fed ethylene production units (or crackers) contains valuable C5 diolefins such as cis and trans 1,3 Pentadiene (otherwise known as Piperylenes or "Pips"), Isoprene, and Cyclopentadiene (CPD). Current processes in the field are focused on isolating the isoprene from this mixture for making poly isoprene. The heavies such as cis and trans 1,3 pentadienes and the dimer of cyclopentadiene (known as dicyclopentadiene or DCPD) are normally destroyed via hydrogenation either to be blended with gasoline or to recycle as a feed to the cracker. The art of separation has been well known for many decades and uses equipment such as dimer reactors, distillation columns, and extractive distillation methods to obtain the polymer grade isoprene with maximum recovery of isoprene.

DCPD and the 1,3 pentadienes are used as feed stocks in the hydrocarbon resin manufacturing industry. The compositions of these two feed stocks vary depending on the processing details of each liquid cracker. The type of hydrocarbon resin manufactured and is well known to those in the art of making hydrocarbon resins. The piperylene stream traditionally obtained from the C5 fraction does not contain other key reactive monomers essential for making catalytic C5 hydrocarbon resins. Further, the DCPD stream is traditionally operated in a way that minimizes formation of CPD codimers. In fact, the C5 separations design is such that the dimerization system is targeted to minimize the codimers and subsequent loss of isoprene. The design of the C5 separations units is intended for maximum isoprene recovery and heavy molecules such as DCPD and Piperylene are generally rejected/lost in the process of purifying the isoprene.

Isoprene purification systems traditionally involve 2 stage extractive distillation and a sequence of at least 3 purification columns and water wash towers. The products other than isoprene are typically required to be passed through hydrogenation step to saturate problematic alkynes. Prior art processes either concentrate on isoprene purification or removal of alkynes by hydrogenation to upgrade the stream quality. The prior art processes consider the isoprene recovery and DCPD and 1,3 pentadiene recovery in a single coordinated process.

FIELD OF INVENTION

The claimed invention and the apparatuses and methods are intended to obtain DCPD and piperylene streams containing other valuable key reactive mono and diolefins which are required hydrocarbon resin precursors components, that are already present in the C5 fraction, but are lost or ignored, offers flexibility and ease to separate the DCPD and 1,3 pentadienes, provides considerable capacity and operating benefit to downstream hydrogenation units simultaneously increasing the value of byproducts without hydrogenation being required. Such apparatuses and methods would allow more efficient operation and system design and operating conditions producing a minimum of four valuable streams from the C5 fraction of the Pyrolysis Gasoline.

SUMMARY OF INVENTION

In various embodiments, system of apparatuses and operating conditions for obtaining a hydrocarbon resin grade DCPD stream, a hydrocarbon resin grade piperylene stream and crude isoprene stream are disclosed. The apparatuses comprise of a distillation column, a sequence of minimum of two dimer reactor systems, with each system having more than one dimer drum in parallel arrangement, heat exchangers in front of dimer systems, distillation columns followed by a dimer system and a minimum of one distillation column.

In other various embodiments, methods for obtaining polymer grade isoprene from the crude isoprene, and the production of sulfur free, high quality gasoline value stream are disclosed. The apparatuses comprise of: a first extractive distillation system comprising of extractive distillation and solvent recovery column, impurity removal system, comprising of sulfur removal system, color removal system, acetylene hydrogenation system, distillation column, a second extractive distillation system, and a minimum of one distillation column and solvent regeneration system comprising of vessels and distillation column.

In other various embodiments, methods to concentrate the CPD in the recycle streams, to recover high value reactive monomers and diolefins into the piperylene stream, and flexibility to either increase the value of the DCPD stream or to recover the isoprene are disclosed.

The foregoing has outlined rather broadly the features of the present disclosure in order that the detailed description that follows may be better understood. Additional features and advantages of the disclosure will be described hereinafter, which form the subject of the claims.

BRIEF DESCRIPTION OF THE DRAWINGS

For a more complete understanding of the present disclosure, and the advantages thereof, reference is now made to the following descriptions to be taken in conjunction with the accompanying drawings describing specific embodiments of the disclosure, wherein:

FIG. 3 shows the various fractions of components that can be obtained by the processes of the claimed invention.

DETAILED DESCRIPTION OF EXEMPLARY EMBODIMENTS

Figure 1:
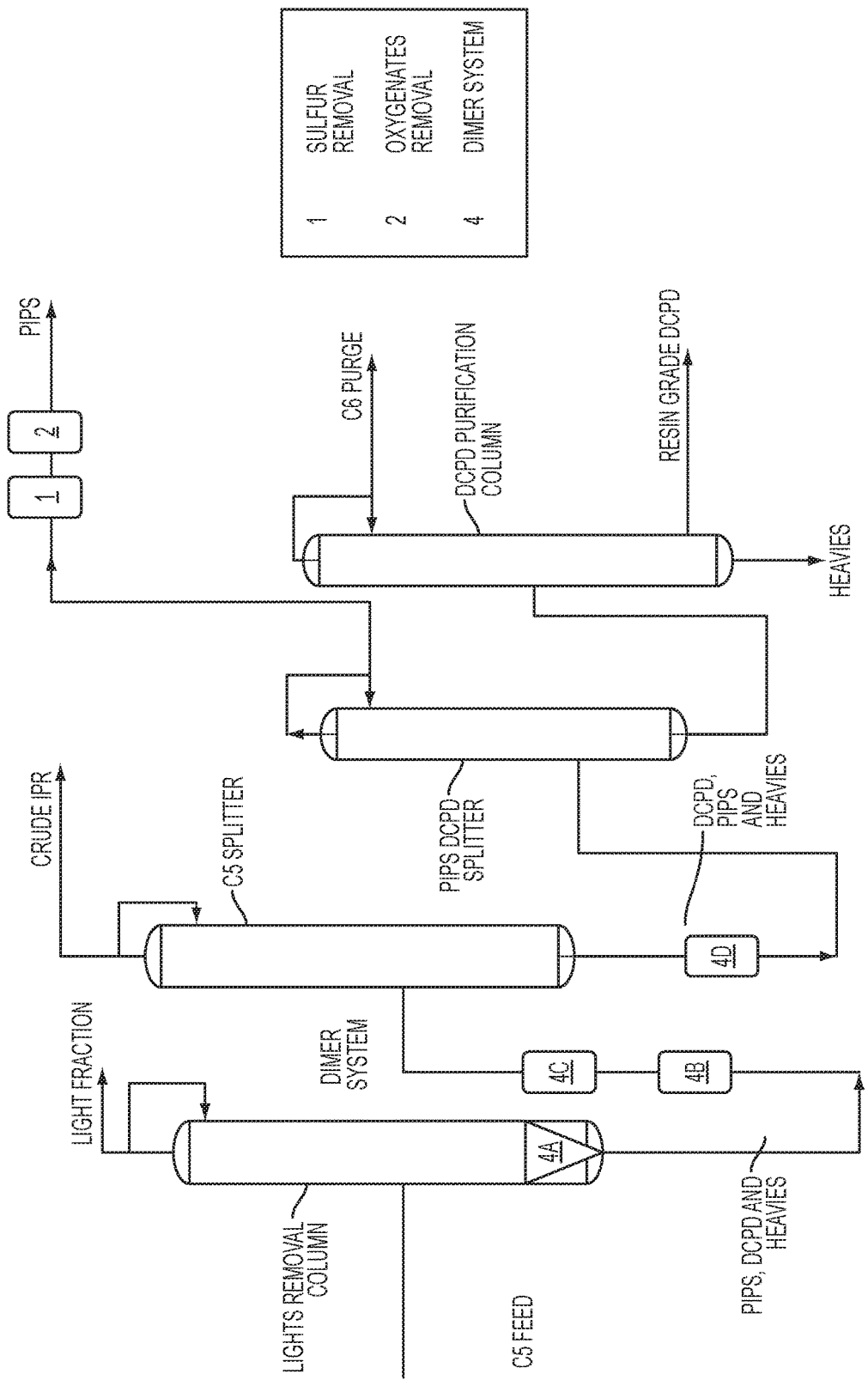
FIG. 1 shows an illustrative hydrocarbon resin feed stock grade DCPD and Piperylenes production system.

In the following description, certain details are set forth such as specific quantities, sizes, etc. so as to provide a thorough understanding of the present embodiments disclosed herein. However, it will be obvious to those skilled in the art that the present disclosure may be practiced without such specific details. In many cases, details concerning such considerations and the like have been omitted inasmuch as such details are not necessary to obtain a complete understanding of the present disclosure and are within the ability of persons of ordinary skill in the relevant art.

Referring to the drawings in general, it will be understood that the illustrations are for the purpose of describing a particular embodiment of the disclosure and are not intended to be limiting thereto. The drawings are not necessarily to scale.

While most of the terms used herein will be recognizable to those of skill in the art, it should be understood, however, that when not explicitly defined, terms should be interpreted as adopting a meaning presently accepted by those of skill in the art.

"Raffinate," as used herein, refers to, for example, light hydrocarbons; "Dimers" and as used herein, refers to DCPD, the dimer of CPD, "Codimers" as used herein, refer to CPD-Isoprene, CPD-Piperylene and CPD- Methyl Cyclopentadiene and to associated trimers, tetramers molecules containing various combinations of three or four molecules of CPD, Isoprene, Piperylene and/or Methyl Cyclopentadiene.

In the thermal cracking in the presence of steam of liquid fractions of petroleum, such as LPG, Naphtha, Diesel and heavies for production of ethylene and or propylene, a hydrocarbon liquid fraction called Pyrolysis Gasoline, is produced. This Pyrolysis Gasoline consists of hydrocarbon components ranging from 4 carbon atoms to more than 10 carbon atoms. Among these, of importance to the field of innovation are mono olefins and diolefins such as cyclopentadiene (CPD), methyl cyclopentadiene, cis and/or trans 1,3 pentadienes (Pips), Isoprene, 2-methylbutene-1,2-methylbutene-2, cyclopentene and similar hydrocarbon molecules containing 5 carbons. These compounds are used for making hydrocarbon resins that are used in wide variety of industries. Isoprene is used predominantly to make rubber and in certain block copolymers.

In various embodiments, apparatuses for obtaining streams consisting of single component or components necessary for making specific catalytic and thermal hydrocarbon resins are disclosed. The apparatuses comprise: distillation columns, a sequence of at least two dimer reactor systems, with each system having at least two dimer drums in parallel arrangement, heat exchangers in front of dimer systems, distillation columns followed by dimer system and a minimum of one distillation column. The apparatuses are operated continuously.

An embodiment of the invention is directed to a process for the production of DCPD and Piperylenes and Isoprene, using a system that employs a specific arrangement of dimerization reactors and operating conditions to enhance the production of DCPD, while at the same time recovering certain precursors for hydrocarbon resin production. As set forth in FIG. 1, the process employs a deisopentanizer (lights removal column) to remove the isopentane from a C5 feed. The recovered isopentane is separated in the lights fraction from the remainder of the process. The remaining C5 feed is passed through a first dimerization system having conditions that are optimized for the enhanced production of DCPD. As shown in FIG. 1, the first dimerization system includes dimer drum 4A, dimer drum 4B, and dimer drum 4C. The dimerized mixture is passed through a C5 splitter column where crude isoprene is extracted overhead. The bottoms product from the C5 splitter column is passed through a second dimerization system followed by passage through a Pips column where Pips are extracted. As shown in FIG. 1, the second dimerization system includes a dimer drum 4D. The bottoms fraction from the Pips column is passed through a DCPD column where the DCPD is extracted. Additionally, the C5 splitter column conditions are optimized to recover increased amounts of 2-methyl butene-2 (2MB2) in the Pips extraction, which serves as a valuable monomer in the production of hydrocarbon resins.

The crude isoprene fraction is subsequently subjected to a fractionation process that involves a two stage extractive distillation column/solvent recovery column (EDC/SRC) system having an impurity removal system and a raw isoprene fractionation system that is present between the first and second EDC/SRC systems.

In various embodiments of the apparatuses, the dimer system consists of either a vessel with overhead vent control with or without an exchanger for temperature control, or isothermal heat exchanger with a vaporizing medium on the shell side, or a tank with circulation pumps for temperature control and mixing, or spheres with agitators or any two of the above in combination. Unlike the present invention, which concentrates on maximizing the DCPD yield minimizing the isoprene loss to dimerization, a set of 2 or 3 parallel dimer drums are arranged in sequence with adequate controls and by-pass mechanisms to modify and control the amount of CPD-isoprene CPD-Pips codimers and Isoprene self dimers along with the DCPD yield.

In various embodiments, the dimer drums, are operated between 60° C. to 130° C. at a pressure consistent to keep the system in liquid phase. Unlike the typical dimer drums the conversion of isoprene to codimers and self dimers are controlled to get required amount of thermal hydrocarbon resin precursors simultaneously achieving maximum kinetically possible conversion of CPD and minimizing the loss of isoprene to heavies.

In various embodiments, the apparatuses further comprise a distillation column "C5 splitter" downstream of the dimer drums to separate the cis/trans pentadienes, and C10 and C11 dimers and codimers from the isoprene stream. The focus of the present invention is to design this column, such that isoprene is free of all the high boiling components starting from CPD and with minimum capital and energy consumption. The disadvantage of the previous designs is that the Piperylenes stream becomes devoid of certain key monomers and di-olefins (such as Cyclopentene, 2-methylbutene-1,2-methybutene-2 and similar reactive species or precursors that are of high value to making hydrocarbon resins. Further, some of these components go with crude isoprene stream from the top of the C5 splitter and increases the energy and capital costs along with land requirements within the isoprene extraction system. Further, these components can cause the operational and metallurgical issues in the Isoprene extraction section due to their relative reactive tendency. In the present invention the C5 splitter typically consists of trays or packing, providing a minimum of 75 to 85 theoretical stages. The operating pressure of the present system is set such that the overhead temperature is maintained between 55° C. to 70° C. and requires only air cooling. The feed location and the operation is set such that all the key mono-olefins and di-olefins boiling higher than isoprene, except isoprene are recovered at the bottom of the distillation column and isoprene and lighter or similar boiling components are recovered at the top. The slip of isoprene to the bottom is controlled such that piperylenes stream meets the required isoprene content for resin making, which is typically in the range of 0.0 to 2 percent by weight depending on the type of C5 hydrocarbon resin being manufactured.

In various embodiments, the apparatus C5 splitter is followed by a dimer drum that is operated at a temperature typically in the range of 80° C. to 130° C., to dimerize all the unconverted CPD into DCPD and codimers with isoprene. The dimer drum is operated such that the Pips stream meets the specification on CPD and isoprene, simultaneously providing valuable codimer hydrocarbon resin precursors components to DCPD stream.

In various embodiments, the dimer drum above is followed by a minimum of one distillation column to a maximum of 2 distillation columns operated in vacuum and at temperatures not exceeding 130° C. at the highest point in the distillation column to obtain Pips and DCPD streams meeting the catalytic C5 hydrocarbon resin feed and thermal hydrocarbon resin feed quality, respectively. The Pips stream is taken as the product from the overhead of the first distillation column and the DCPD stream is drawn either as a side product or bottom product from the second distillation column.

In various embodiments, the Pips stream from the Pips/DCPD splitter is subject to sulfur removal and water wash to remove the bisulfides and oxygenates, which are detrimental to the hydrocarbon resin process. Further the Pips stream may or may not be subjected to drying for removing the moisture, either as part of oxygenates removal system or separately.

Figure 2:
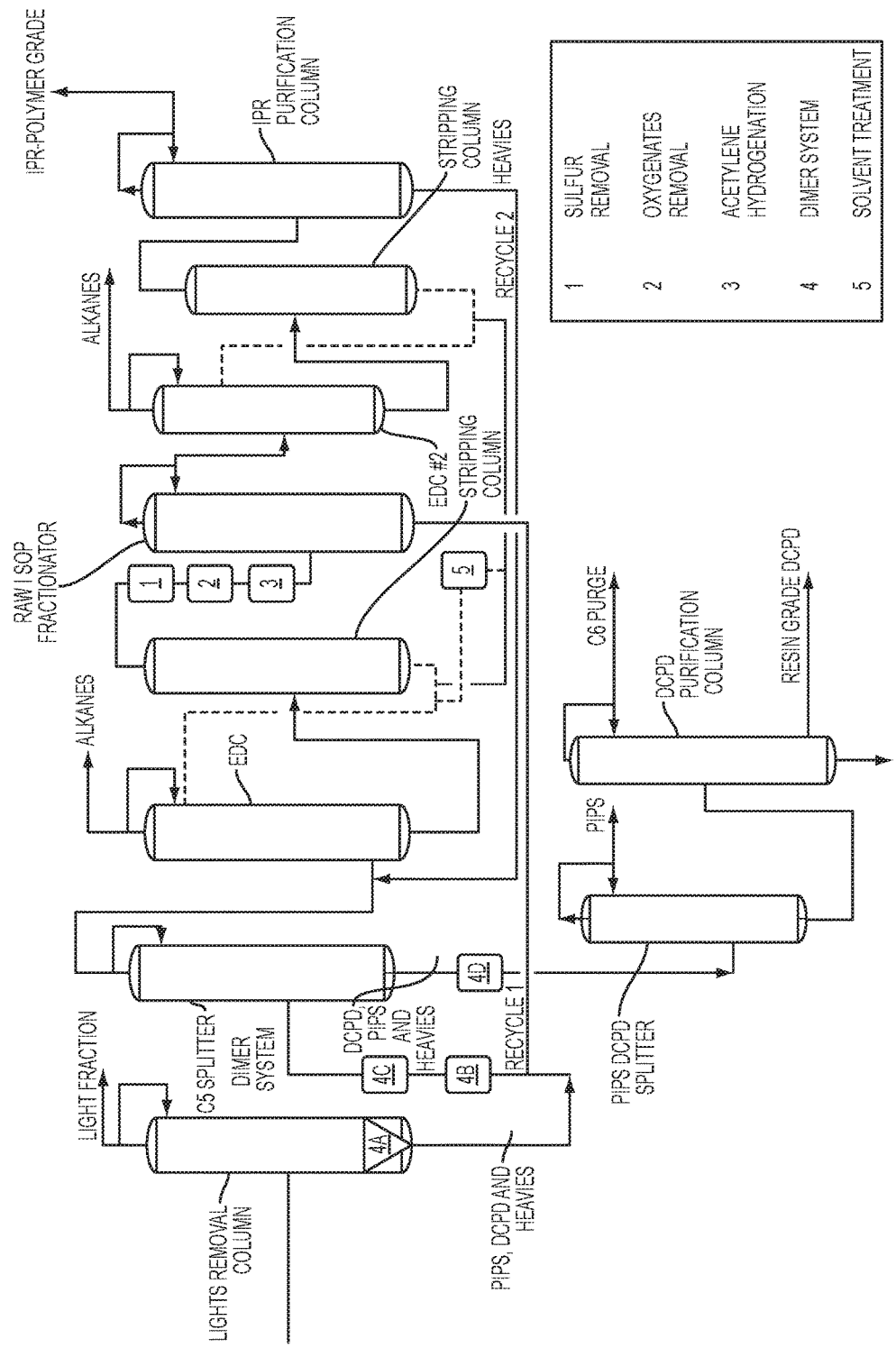
FIG. 2 shows an illustrative coupling of an isoprene extraction system to a hydrocarbon resin grade piperylenes and DCPD separation system.

FIG. 2 illustrates the coupling of the isoprene extraction unit with the C5 separations unit as described above and in FIG. 1 for producing polymer grade isoprene and also simultaneously producing hydrocarbon resin grade DCPD and C5 hydrocarbon resin feed stock, thereby increasing the net value of the C5 olefins and di-olefins present in the C5 fraction of pyrolysis gasoline.

In various embodiments, the arrangement of dimers and recycle streams from the isoprene extraction unit provide unique opportunity and flexibility to concentrate the CPD stream and convert that CPD into DCPD with minimum recycle lines, and also provides flexibility to obtain maximum value for the isoprene either through hydrocarbon resin feed stocks or through polymer grade isoprene. Current art involves a series of more than one recycle and up to 5 recycle streams of light and heavy component streams containing concentrated isoprene and hence increase the net capital and energy costs. This innovation minimizes the recycle streams to maximum of two and hence reduces the capital and energy costs.

In various embodiments, the isoprene extraction system consists of two extractive distillation columns, two solvent recovery columns, one raw isoprene fractionator and one isoprene purification column and a sulfur removal unit, an oxygenates removal unit, and an acetylene removal unit.

In various embodiments, the arrangement of the isoprene extraction system (with two stage Extractive distillation with an impurity removal system located between the two extraction systems) provides the flexibility to concentrate the CPD lost to isoprene section from C5 Splitter and such that the CPD is recycled back to dimer system to maximize the DCPD yield and quantity. This feature minimizes the number of recycle loops compared to traditional systems. Further, the CPD conversion achieved in the dimer system also increases due to higher CPD concentration, unlike traditional systems. The impurity removal system is small due to its location and achieves the removal of Sulfur, Alkynes, and Oxygenates which is unique.

In various embodiments, the above feature also reduces the size of the second stage extractive distillation size compared to traditional designs and reduces the number of purification distillation columns to either one or none and polymer grade isoprene is achieved with minimum of capital and operating cost.

In various embodiments, the bottom of the lights removal column is also designed such that the dimerization of CPD to DCPD is controlled and this in turn reduces the number of dimer drums, and reduces the quantity of unwanted trimers and heavies that form in the current art.

FIG. 3 illustrates the various fractions of components that can be obtained by the processes of the claimed invention. For example, the M12 stream contains largely only isoprene and the M6 fraction contains predominantly DCPD. The processes of the claimed invention are advantageous in that they From the foregoing description, one skilled in the art can easily ascertain the essential characteristics of this disclosure, and without departing from the spirit and scope thereof, can make various changes and modifications to adapt the disclosure to various usages and conditions. The embodiments described herein above are meant to be illustrative only and should not be taken as limiting of the scope of the disclosure, which is defined in the following claims.

What is claimed is:

1. A process for separating dicyclopentadiene (DCPD), piperylenes and isoprene from a C5 feed, the process comprising the steps of:
   providing a C5 feed comprising isopentane, isoprene, cyclopentadiene, and piperylenes to a lights removal column;
   separating isopentane from the C5 feed into a first lights fraction;
   removing the remaining C5 feed into a first heavy bottoms fraction from the lights removal column;
   feeding the first heavy bottoms fraction to a heat exchanger;
   feeding the first heavy bottoms fraction from the heat exchanger to a first dimerization system to form a dimerized mixture comprising DCPD, isoprene, piperylenes, and unreacted cyclopentadiene;
   passing the dimerized mixture through a C5 splitter column;
   extracting isoprene from the C5 splitter column into a second lights fraction;
   passing the second lights fraction through a two stage extractive distillation column/solvent recovery column system having an impurity removal system and a raw isoprene fractionation system disposed between a first and a second extractive distillation column/solvent recovery column system of the two stage extractive distillation column/solvent recovery column system;
   recycling cyclopentadiene (CPD) from the raw isoprene fractionation system to the first dimer system;
   collecting a second heavy bottoms fraction from the C5 splitter column containing DCPD and piperylenes;
   passing the second heavy bottoms fraction from the C5 splitter column to a second dimerization system;
   passing a fraction comprising DCPD and piperylenes from the second dimerization system to a piperylenes extraction column to extract piperylenes; and
   passing a third heavy bottoms fraction comprising DCPD from the piperylenes extraction column to a DCPD extraction column to extract DCPD;
   wherein the impurity removal system comprises a sulfur removal unit, an oxygenates removal unit, and an acetylene removal unit, each of which are disposed between the first extractive distillation column and the second extractive distillation column of the two stage extractive distillation column/solvent recovery column system.

2. The process of claim 1, wherein the C5 splitter column comprises a minimum of 75 to 85 theoretical stages.

3. The process of claim 1, wherein the process in the C5 splitter column is carried out at an overhead temperature range of 55° C. to 70° C.

4. The process of claim 1, wherein the second dimerization system is operated at a temperature between 80° C. to 130° C.

5. The process of claim 1, further comprising the step of passing the extracted isoprene through an isoprene extraction unit to produce polymer grade isoprene.

6. The process of claim 1, further comprising removing bisulfides and oxygenates from the piperylenes from the piperylenes extraction column.

7. The process of claim 1, wherein the first dimerization system comprises at least two dimer drums arranged in a parallel arrangement.

8. The process of claim 1, wherein the second dimerization system comprises at least two dimer drums arranged in a parallel arrangement.

9. The process of claim 1, wherein the first dimer system comprises a vessel with overhead vent control and an exchanger for temperature control.

10. The process of claim 1, wherein the first dimer system comprises an isothermal heat exchanger with a vaporizing medium on a shell side of the of the isothermal heat exchanger.

11. The process of claim 1, wherein the first dimer system comprises a tank with circulation pumps for temperature control and mixing.

* * * * *